(12) United States Patent
Connaughton et al.

(10) Patent No.: US 12,397,119 B2
(45) Date of Patent: Aug. 26, 2025

(54) MEDICATION DELIVERY DEVICE WITH SENSING SYSTEM

(71) Applicant: Eli Lilly and Company, Indianapolis, IN (US)

(72) Inventors: Eoin Patrick Connaughton, County Wexford (IE); Brendan Francis Laurenzi, Rutland, MA (US); Vincent Patrick Thomas Lawlor, Dublin (IE); Patrick Kevin Murphy, Allston, MA (US); Sean Matthew Pszenny, Cambridge, MA (US); Oliver Brian Regele, Cambridge, MA (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 926 days.

(21) Appl. No.: 17/434,093

(22) PCT Filed: Feb. 20, 2020

(86) PCT No.: PCT/US2020/018957
§ 371 (c)(1),
(2) Date: Aug. 26, 2021

(87) PCT Pub. No.: WO2020/176317
PCT Pub. Date: Sep. 3, 2020

(65) Prior Publication Data
US 2022/0118194 A1    Apr. 21, 2022

Related U.S. Application Data

(60) Provisional application No. 62/811,194, filed on Feb. 27, 2019.

(51) Int. Cl.
*A61M 5/315* (2006.01)

(52) U.S. Cl.
CPC .... *A61M 5/31585* (2013.01); *A61M 5/31528* (2013.01); *A61M 5/31551* (2013.01);
(Continued)

(58) Field of Classification Search
CPC .......... A61M 5/31585; A61M 5/31528; A61M 5/31551; A61M 2205/3317;
(Continued)

(56) References Cited

U.S. PATENT DOCUMENTS

| 3,591,100 A | 7/1971 | Itoh et al. |
| 5,509,905 A | 4/1996 | Michel |

(Continued)

FOREIGN PATENT DOCUMENTS

| CA | 3073279 | 2/2019 |
| CN | 108030978 A | 5/2018 |

(Continued)

OTHER PUBLICATIONS

Patent Cooperation Treaty International Search Report pertaining to International Application No. PCT/US2020/018953; International Filing Date: Feb. 20, 2020; Date of Mailing: Apr. 20, 2020.

(Continued)

*Primary Examiner* — Dung T Ulsh
*Assistant Examiner* — Nelson Louis Alvarado, Jr.
(74) *Attorney, Agent, or Firm* — Arthur Shum

(57) ABSTRACT

Medication delivery devices are provided having a dose delivery sensing capability. A dose button includes a support and a cover that at least partially encloses an electronics assembly including a sensor for detecting rotation of a component during dose delivery to determine a dosage of delivered medication. The electronics assembly includes a controller for receiving a signal from the sensor. The medi- (Continued)

cation delivery device may be configured to communicate dosage delivery information to an external device.

25 Claims, 9 Drawing Sheets

(52) U.S. Cl.
    CPC ............... *A61M 2205/3317* (2013.01); *A61M 2205/3327* (2013.01); *A61M 2207/00* (2013.01)

(58) Field of Classification Search
    CPC ...... A61M 2205/3327; A61M 2207/00; A61M 2205/50; A61M 5/3156; A61M 5/31535; A61M 5/31568; A61M 2205/3576
    See application file for complete search history.

(56) References Cited

U.S. PATENT DOCUMENTS

| | | | |
|---|---|---|---|
| 5,536,240 A | 7/1996 | Edwards et al. | |
| 5,536,249 A | 7/1996 | Castellano et al. | |
| 5,728,074 A | 3/1998 | Castellano et al. | |
| 5,951,398 A | 9/1999 | Yamamoto et al. | |
| 6,138,669 A | 10/2000 | Rocci, Jr. et al. | |
| 6,277,099 B1* | 8/2001 | Strowe | A61M 5/3158 604/207 |
| 6,585,698 B1 | 7/2003 | Packman et al. | |
| 7,008,399 B2 | 3/2006 | Larsen et al. | |
| 7,195,616 B2 | 3/2007 | Diller et al. | |
| 7,291,132 B2 | 11/2007 | DeRuntz et al. | |
| 7,740,612 B2 | 6/2010 | Hochman | |
| 7,749,786 B2 | 7/2010 | Wells | |
| 8,221,356 B2 | 7/2012 | Enggaard et al. | |
| 8,257,319 B2 | 9/2012 | Plumptre | |
| 8,556,865 B2 | 10/2013 | Krulevitch et al. | |
| 8,579,867 B2 | 11/2013 | Harms et al. | |
| 8,734,394 B2 | 5/2014 | Adams et al. | |
| 9,078,973 B2 | 7/2015 | Harms et al. | |
| 9,186,465 B2 | 11/2015 | Jorgensen et al. | |
| 9,345,838 B2 | 5/2016 | Plumptre | |
| 9,616,178 B2 | 4/2017 | Butler et al. | |
| 9,636,464 B1 | 5/2017 | Binier | |
| 9,649,448 B2 | 5/2017 | Madsen | |
| 9,675,761 B2 | 6/2017 | Hoeholt et al. | |
| 9,750,886 B2 | 9/2017 | Plambech et al. | |
| 9,764,095 B2 | 9/2017 | Draper | |
| 9,833,576 B2 | 12/2017 | Windum et al. | |
| 10,004,852 B2 | 6/2018 | Marsh et al. | |
| 10,179,207 B2 | 1/2019 | Haupt | |
| 10,383,996 B2 | 8/2019 | Miller et al. | |
| 10,420,895 B2 | 9/2019 | Erbstein et al. | |
| 10,420,897 B2 | 9/2019 | Veasey et al. | |
| 10,682,469 B2 | 6/2020 | Jakobsen et al. | |
| 10,909,217 B2 | 2/2021 | Gerken | |
| 11,052,198 B2 | 7/2021 | Madsen et al. | |
| 11,471,608 B2 | 10/2022 | Byerly et al. | |
| 11,638,785 B2 | 5/2023 | Byerly et al. | |
| 2001/0034506 A1 | 10/2001 | Hirschman et al. | |
| 2002/0120655 A1 | 8/2002 | Liu et al. | |
| 2003/0005891 A1 | 1/2003 | Lu | |
| 2004/0210199 A1 | 10/2004 | Atterbury et al. | |
| 2006/0153693 A1 | 7/2006 | Fiechter et al. | |
| 2006/0206057 A1* | 9/2006 | DeRuntz | A61M 5/31551 604/224 |
| 2009/0069742 A1 | 3/2009 | Larsen | |
| 2011/0270214 A1 | 11/2011 | Jorgensen et al. | |
| 2014/0074041 A1 | 3/2014 | Pedersen et al. | |
| 2014/0194829 A1 | 7/2014 | Baek et al. | |
| 2014/0276583 A1 | 9/2014 | Chen et al. | |
| 2014/0312074 A1 | 10/2014 | Madsen et al. | |
| 2015/0032059 A1 | 1/2015 | Allerdings et al. | |
| 2015/0290396 A1 | 10/2015 | Nagar et al. | |
| 2015/0367077 A1 | 12/2015 | Plambech et al. | |
| 2016/0008552 A1 | 1/2016 | Madsen et al. | |
| 2016/0012205 A1* | 1/2016 | Saint | H04B 7/24 604/189 |
| 2016/0030680 A1 | 2/2016 | Veasey et al. | |
| 2016/0030683 A1 | 2/2016 | Taylor et al. | |
| 2016/0082192 A1 | 3/2016 | Veasey et al. | |
| 2016/0175527 A1 | 6/2016 | McCullough | |
| 2016/0213853 A1 | 7/2016 | Despa et al. | |
| 2016/0239610 A1 | 8/2016 | Andersen | |
| 2016/0287804 A1 | 10/2016 | Madsen et al. | |
| 2016/0287807 A1 | 10/2016 | Madsen et al. | |
| 2016/0378951 A1 | 12/2016 | Gofman et al. | |
| 2017/0368263 A1 | 12/2017 | Ploch | |
| 2018/0126088 A1 | 5/2018 | Radmer et al. | |
| 2018/0147363 A1 | 5/2018 | Hansen et al. | |
| 2018/0353700 A1 | 12/2018 | Säll et al. | |
| 2018/0369488 A1 | 12/2018 | Carlsson et al. | |
| 2018/0369494 A1 | 12/2018 | Grubbe | |
| 2019/0022328 A1* | 1/2019 | Schleicher | A61M 5/20 |
| 2019/0022330 A1 | 1/2019 | Schleicher et al. | |
| 2019/0054251 A1 | 2/2019 | Pieronek et al. | |
| 2019/0083708 A1 | 3/2019 | Säll | |

FOREIGN PATENT DOCUMENTS

| | | |
|---|---|---|
| CN | 108392698 A | 8/2018 |
| CN | 105263546 B | 7/2019 |
| EP | 2060284 | 5/2009 |
| EP | 3162398 | 5/2017 |
| JP | A2004526486 | 9/2004 |
| JP | 2015527128 A | 9/2015 |
| JP | 2017500090 A | 1/2017 |
| JP | A2019500968 | 1/2019 |
| RU | 2535601 C1 | 12/2014 |
| WO | 1990009202 | 8/1990 |
| WO | 1996019872 | 6/1996 |
| WO | WO200264196 | 8/2002 |
| WO | 2003005891 | 1/2003 |
| WO | 2006045525 | 5/2006 |
| WO | 2009062675 | 5/2009 |
| WO | 2014020008 A1 | 2/2014 |
| WO | 2014180744 | 11/2014 |
| WO | 2015075136 A1 | 5/2015 |
| WO | WO2016007935 | 1/2016 |
| WO | 2016180873 | 11/2016 |
| WO | 2016193229 | 12/2016 |
| WO | 2016198516 A1 | 12/2016 |
| WO | 2017092960 | 6/2017 |
| WO | 2017097507 | 6/2017 |
| WO | 2017106224 A1 | 6/2017 |
| WO | 2017114768 | 7/2017 |
| WO | 2017120178 A1 | 7/2017 |
| WO | WO2017118705 | 7/2017 |
| WO | 2017148855 | 9/2017 |
| WO | 2017200989 A1 | 11/2017 |
| WO | 2018013419 | 1/2018 |
| WO | 2018099795 | 6/2018 |
| WO | 2018104289 | 6/2018 |
| WO | 2018125887 | 7/2018 |
| WO | 2018138016 | 8/2018 |
| WO | 2018141571 | 8/2018 |
| WO | 2019018793 A1 | 1/2019 |
| WO | WO201936576 | 2/2019 |
| WO | 2019121610 A1 | 6/2019 |

OTHER PUBLICATIONS

Patent Cooperation Treaty Written Opinion of the International Searching Authority pertaining to International Application No. PCT/US2020/018953; International Filing Date: Feb. 20, 2020; Date of Mailing: Apr. 20, 2020.
Patent Cooperation Treaty International Search Report pertaining to International Application No. PCT/US2020/018957; International Filing Date: Feb. 20, 2020; Date of Mailing: May 25, 2020.
Patent Cooperation Treaty Written Opinion of the International Searching Authority pertaining to International Application No.

(56) References Cited

OTHER PUBLICATIONS

PCT/US2020/018957; International Filing Date: Feb. 20, 2020; Date of Mailing: May 25, 2020.

* cited by examiner

MEDICATION DELIVERY DEVICE WITH SENSING SYSTEM

BACKGROUND

Patients suffering from various diseases must frequently inject themselves with medication. To allow a person to conveniently and accurately self-administer medicine, a variety of devices broadly known as pen injectors or injection pens have been developed. Generally, these pens are equipped with a cartridge including a piston and containing a multi-dose quantity of liquid medication. A drive member is movable distally to advance the piston in the cartridge to dispense the contained medication from an outlet at the distal cartridge end, typically through a needle.

In disposable or prefilled pens, after a pen has been utilized to exhaust the supply of medication within the cartridge, a user discards the entire pen and begins using a new replacement pen. In reusable pens, after a pen has been utilized to exhaust the supply of medication within the cartridge, the pen is disassembled to allow replacement of the spent cartridge with a fresh cartridge, and then the pen is reassembled for its subsequent use.

Many pen injectors and other medication delivery devices utilize mechanical systems in which members rotate and/or translate relative to one another in a manner proportional to the dose delivered by operation of the device. Systems to measure the relative movement of members of a medication delivery device have been developed in order to assess the dose delivered. Yet, systems integrated into the device or module for high volume manufacturing and repeatable accuracy during the product's lifecycle have been challenging to design. The administration of a proper amount of medication requires that the dose delivered by the medication delivery device be accurate. Many pen injectors and other medication delivery devices do not include the functionality to automatically detect and record the amount of medication delivered by the device during the injection event. In the absence of an automated system, a patient must manually keep track of the amount and time of each injection.

The inventors have recognized a need for a device that is operable to automatically detect the dose delivered by the medication delivery device during an injection event, and/or overcome one or more of these and other shortcomings of the prior art.

SUMMARY

The present disclosure relates to an electronic dose detection system for a medication delivery device positioned at a proximal portion of a medication delivery device. The dose delivery detection system is operable to detect data for determining the amount of a dose of medication delivered by the medication delivery device.

In one embodiment, a medication delivery device is provided, including a housing, an outlet, and a dose button that is axially translatable relative to the housing to activate a dose dispensing mode in which medication is dispensed out of the outlet. The dose button includes a support and a cap coupled to the support. The medication delivery device also includes a compartment defined between the support and the cap, a tubular body that rotates relative to the housing during the dose dispensing mode, and an electronics assembly. The electronics assembly includes a sensor configured to sense rotation of the tubular body and a controller configured to receive a signal from the sensor. At least a portion of the electronic assembly is positioned within the compartment.

In one embodiment, a method of assembling a medication delivery device includes providing a housing, providing an outlet, and coupling a tubular body to the housing. The tubular body is configured to rotate relative to the housing during a dose dispensing mode in which medication is dispensed out of the outlet. The method also includes forming a dose button having a cap and a support by at least partially enclosing an electronics assembly between the cap and the support and attaching the cap to the support. The electronics assembly has a sensor configured to sense rotation of the tubular body. The method also includes configuring the dose button to be axially translatable relative to the housing. Axially translating the dose button relative to the housing activates the dose dispensing mode.

BRIEF DESCRIPTION OF THE DRAWINGS

Additional embodiments of the disclosure, as well as features and advantages thereof, will become more apparent by reference to the description herein taken in conjunction with the accompanying drawings. The components in the figures are not necessarily to scale. Moreover, in the figures, like-referenced numerals designate corresponding parts throughout the different views.

DETAILED DESCRIPTION

Figure 1:
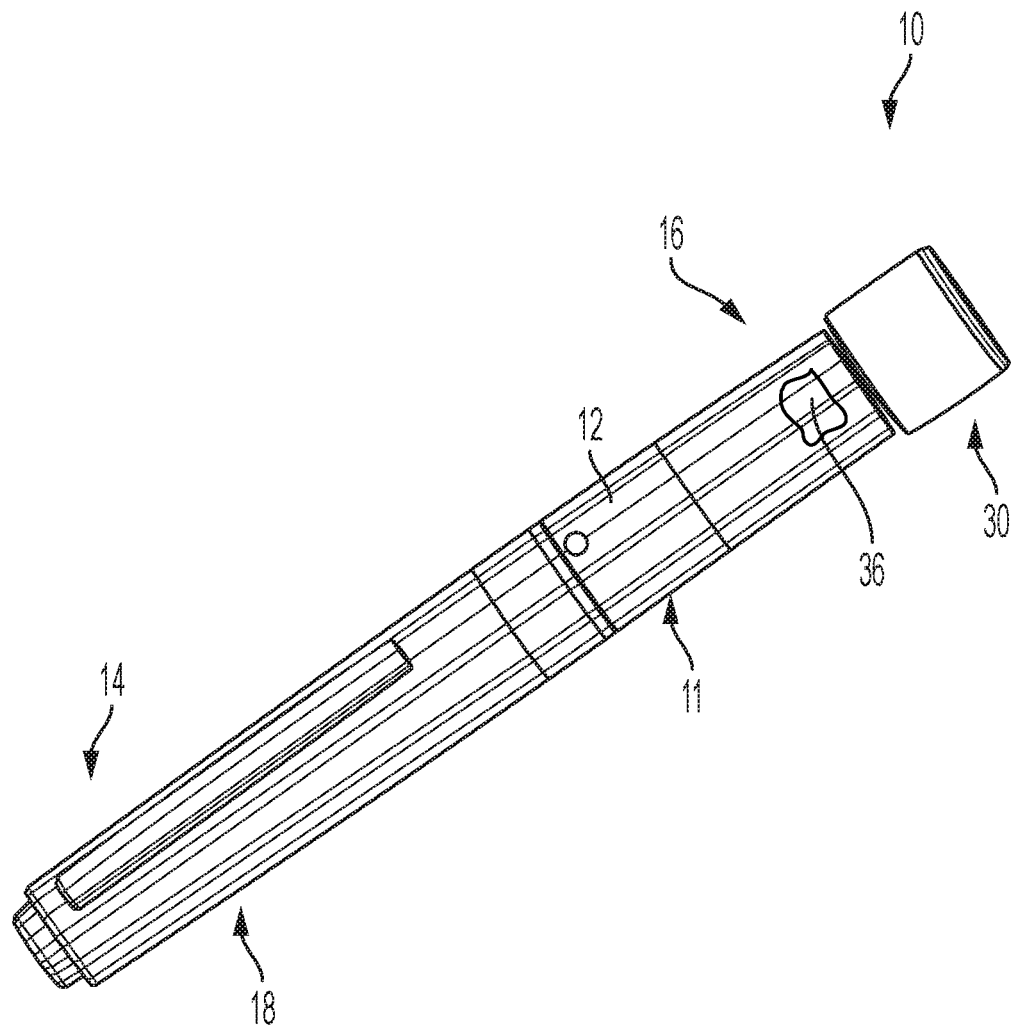
FIG. 1 is a perspective view of a medication delivery device having a dose detection system according to aspects of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the invention is thereby intended.

The present disclosure relates to sensing systems for medication delivery devices. In one aspect, the sensing system is for sensing of relative rotational movement between a dose-setting assembly and an actuator assembly of the medication delivery device in order to determine the amount of a dose delivered by a medication delivery device. The sensed relative rotational movements are correlated to the amount of the dose delivered. By way of illustration, the medication delivery device is described in the form of a pen injector. However, the medication delivery device may be any device which is used to set and to deliver a dose of a medication, such as pen injectors, infusion pumps and syringes. The medication may be any of a type that may be delivered by such a medication delivery device.

Devices described herein may further comprise a medication, such as for example, within a reservoir or cartridge 20. In another embodiment, a system may comprise one or more devices including device 10 and a medication. The term "medication" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by the above device. The medication as used in the device may be formulated with one or more excipients. The device is operated in a manner generally as described above by a patient, caregiver or healthcare professional to deliver medication to a person.

Figure 2:
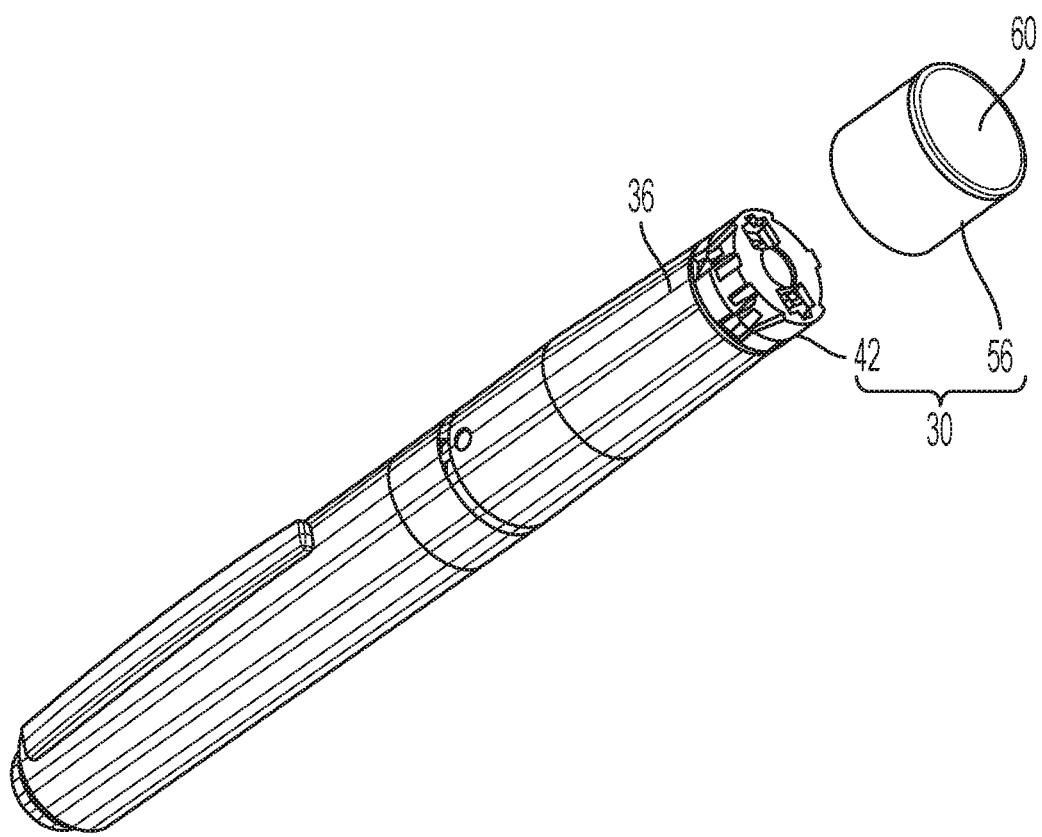
FIG. 2 is a partially exploded perspective view of the medication delivery device of FIG. 1, showing a dose button having a support and a cover, where the cover is shown separated from the support.
Figure 3:
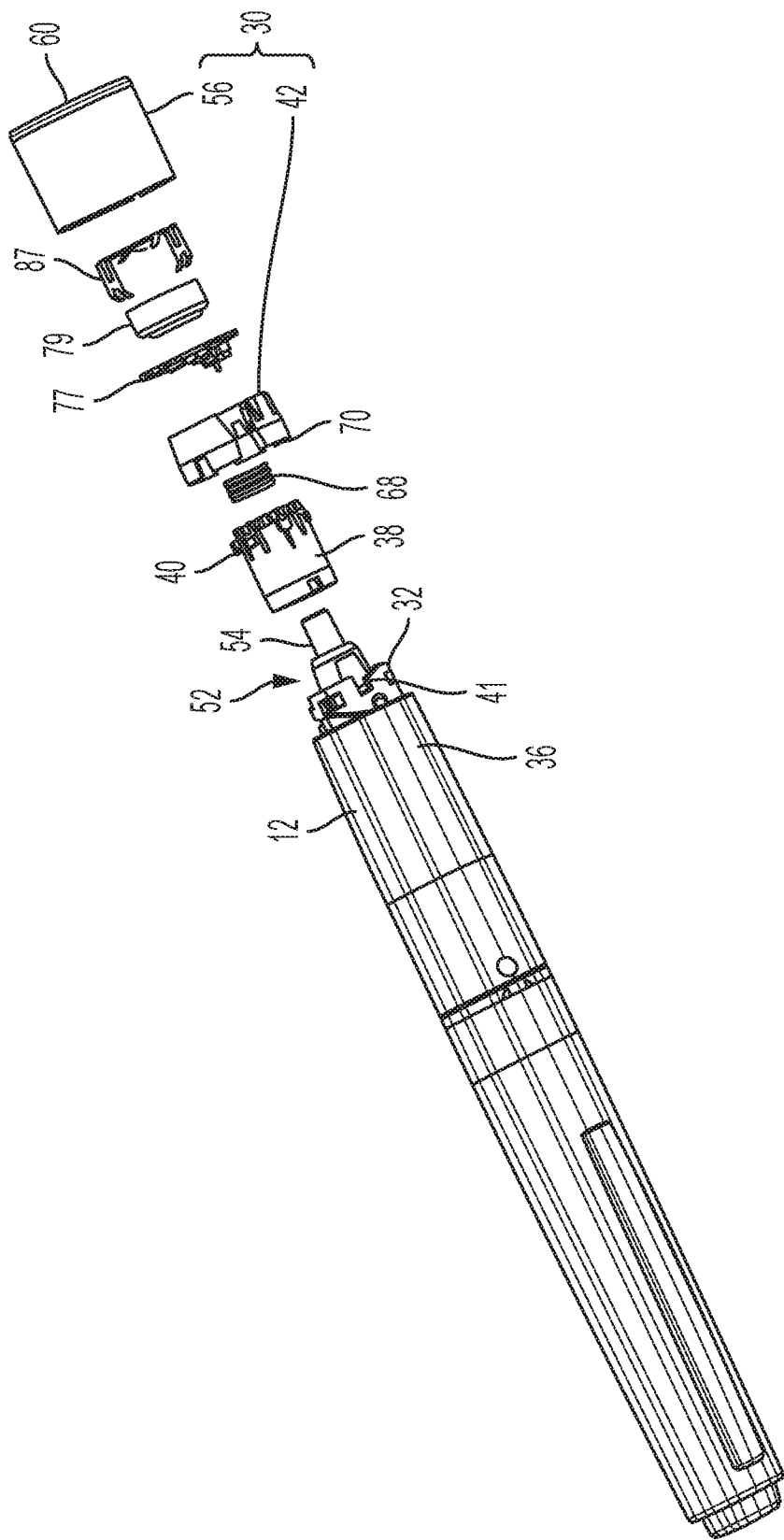
FIG. 3 is a partially exploded side view of the medication delivery device of FIG. 1 showing the components of the dose detection system.
Figure 4:
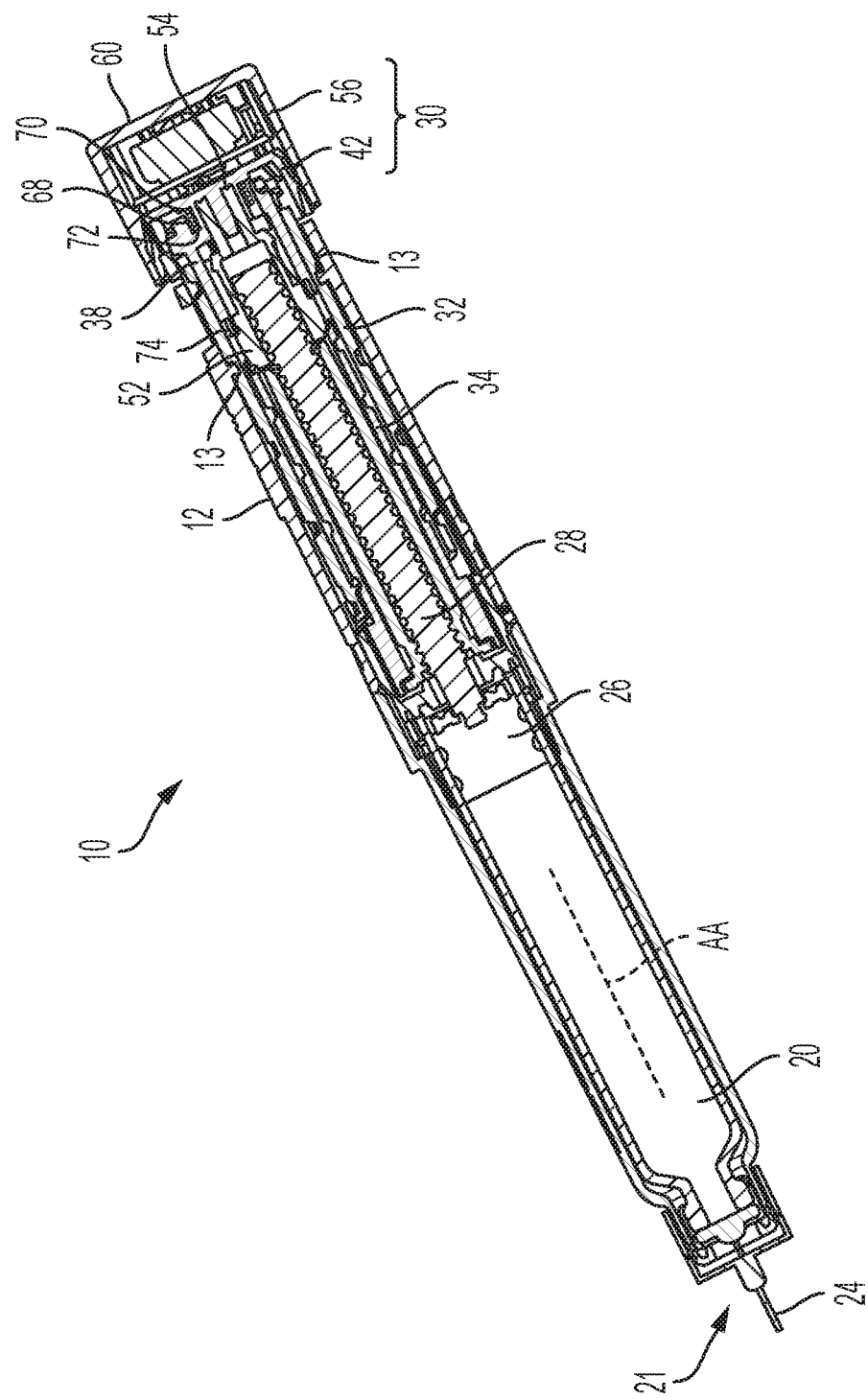
FIG. 4 is a cross-sectional view of the medication delivery device of FIG. 1.

An exemplary medication delivery device 10 is illustrated in FIGS. 1-4 as a pen injector configured to inject a medication into a patient through a needle. Device 10 includes a body 11 that may comprise an elongated, pen-shaped housing 12 including a distal portion 14 and a proximal portion 16. Distal portion 14 may be received within a pen cap 18. Referring to FIG. 4, distal portion 14 may contain cartridge 20 configured to hold the medicinal fluid to be dispensed through the outlet 21 of the housing a dispensing operation. The outlet 21 of distal portion 14 may be equipped with an injection needle 24. In some embodiments, the injection needle is removable from the housing, while some embodiments include a needle fixed to the cartridge unit. In some embodiments, the injection needle is replaced with a new injection needle after each use.

A piston 26 may be positioned in reservoir 20. The medication delivery device may include an injecting mechanism positioned in proximal portion 16 that is operative to advance piston 26 toward the outlet of reservoir 20 during the dose dispensing operation to force the contained medicine through the needled end. The injecting mechanism may include a drive member 28, illustratively in the form of a screw, that is axially moveable relative to housing 12 to advance piston 26 through reservoir 20.

The device may include a dose-setting assembly coupled to the housing 12 for setting a dose amount to be dispensed by device 10. As best seen in FIGS. 3 and 4, in the illustrated embodiment, the dose-setting assembly includes a dose-setting screw 32 and a flange 38. The dose-setting screw 32 is in the form of a screw element operative to spiral (i.e., simultaneously move axially and rotationally) about a longitudinal axis AA of rotation relative to housing 12 during dose setting and dose dispensing. FIGS. 3 and 4 illustrate the dose-setting screw 32 fully screwed into housing 12 at its home or zero dose position. Dose-setting screw 32 is operative to screw out in a proximal direction from housing 12 until it reaches a fully extended position corresponding to a maximum dose deliverable by device 10 in a single injection. The extended position may be any position between a position corresponding to an incremental extended position (such as a dose setting a 0.5 or 1 unit) to a fully extended position corresponding to a maximum dose deliverable by device 10 in a single injection and to screw into housing 12 in a distal direction until it reaches the home or zero position corresponding to a minimum dose deliverable by device 10 in a single injection.

Referring to FIGS. 3 and 4, dose-setting screw 32 includes a helically threaded outer surface that engages a corresponding threaded inner surface 13 of housing 12 to allow dose-setting screw 32 to spiral (i.e. simultaneously rotate and translate) relative to housing 12. Dose-setting screw 32 further includes a helically threaded inner surface that engages a threaded outer surface of sleeve 34 (FIG. 4) of device 10. The sleeve 34 includes internal threads engaged with the external threads of drive member 28, which in turn, when sleeve 34 moving axially, drives drive member 28 axially to move the piston 26. The outer surface of dose-setting screw 32 includes dose indicator markings, such as numbers that are visible through a dosage window 36 to indicate to the user the set dose amount.

As mentioned above, in some embodiments, the dose-setting assembly further includes tubular flange 38 that is coupled in the open proximal end of dose-setting screw 32 and is axially and rotationally locked to the dose-setting screw 32 by protrusions 40 received within openings 41 in the dose-setting screw 32. The protrusions 40 of the flange 38 can be seen in FIGS. 3, 8 and 9, and the openings 41 of the dose-setting screw 32 can be seen in FIG. 3.

As seen in FIGS. 3 and 4, delivery device 10 may include an actuator assembly having a clutch 52 and a dose button 30. The clutch 52 is received within the dose-setting screw 32, and the clutch 52 includes an axially extending stem 54 at its proximal end. The dose button 30 of the actuator assembly is positioned proximally of the dose-setting screw 32 and flange 38. Dose button 30 includes a support 42 and a cap or cover 56. As will be discussed, the support 42 and cover 56 enclose electronics components used to store and/or communicate data relating to amount of dose delivered by a medication delivery device.

The support 42 of the dose button may be attached to the stem 54 of the clutch 52, such as with an interference fit or an ultrasonic weld, so as to axially and rotatably fix together dose button 30 and clutch 52.

Figure 8:
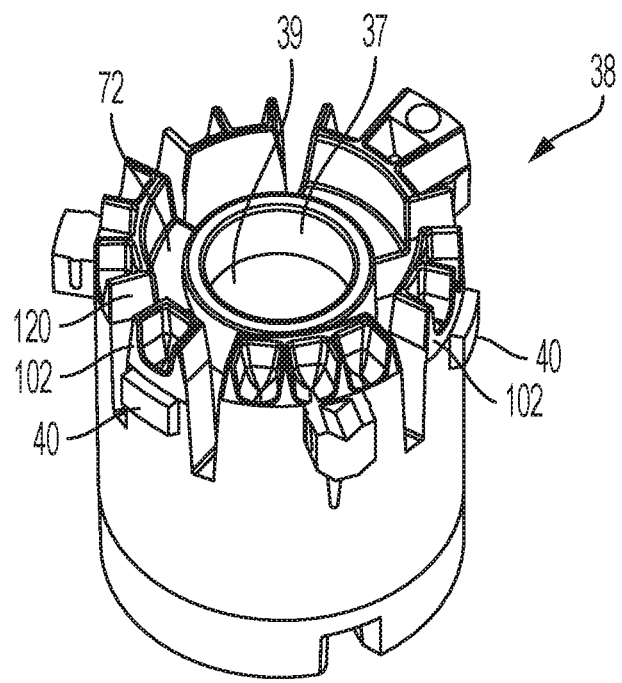
FIG. 8 is a perspective view of a flange of a dose detection system of a medication delivery device.
Figure 9:
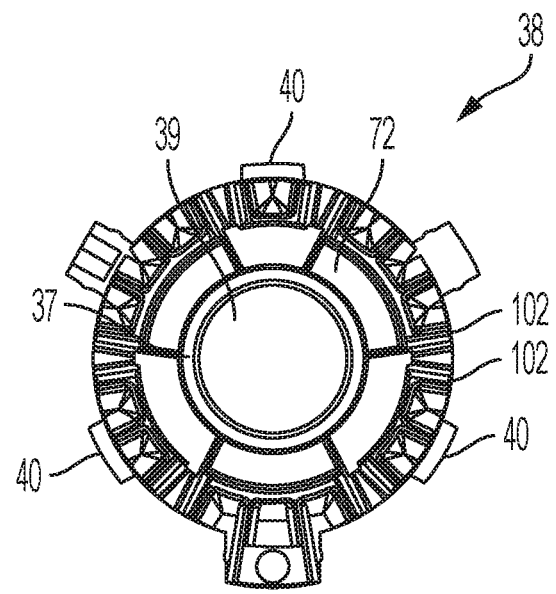
FIG. 9 is a top down view of the flange of FIG. 8.

In some embodiments, a portion of the clutch may pass through a lumen 39 of the flange 38. The lumen 39 of the flange is best seen in FIGS. 8 and 9. The lumen 39 may, in some embodiments, serve to help center the clutch 52 in place.

Proximal face 60 of the dose button 30 may serve as a push surface against which a force can be applied manually, i.e., directly by the user to push the actuator assembly (dose button 30 and clutch 52) in a distal direction. A bias member 68, illustratively a spring, may be disposed between the distal surface 70 of support 42 and a proximal surface 72 of tubular flange 38 (FIGS. 8 and 9) to urge the support 42 of the actuation assembly and the flange 38 of the dose-setting assembly axially away from each other. Dose button 30 is depressible by a user to initiate the dose dispensing operation. In some embodiments, the bias member 68 is seated against this proximal surface 72 and may surround a raised collar 37 of the flange 38.

Delivery device 10 is operable in a dose setting mode and a dose dispensing mode. In the dose setting mode of operation, the dose button 30 is rotated relative to housing 12 to set a desired dose to be delivered by device 10. In some embodiments, rotating the dose button 30 in one direction relative to the housing 12 causes the dose button 30 to axially translate proximally relative to the housing 12, and rotating the dose button 30 in the opposite direction relative to the housing 12 causes the dose button 30 to axially translate distally relative to the housing. In some embodiments, clockwise rotation of the dose button moves the dose button 30 distally, and counter-clockwise rotation of the dose button moves the dose button proximally, or vice versa.

In some embodiments, rotating the dose button 30 to axially translate the dose button 30 in the proximal direction serves to increase the set dose, and rotating the dose button 30 to axially translate the dose button 30 in the distal direction serves to decrease the set dose. The dose button 30 is adjustable in pre-defined rotational increments corresponding to the minimum incremental increase or decrease of the set dose during the dose setting operation. The dose button may include a detent mechanism such that each rotational increment produces an audible and/or tactile "click." For example, one increment or "click" may equal one-half or one unit of medication.

In some embodiments, the set dose amount may be visible to the user via the dial indicator markings shown through a dosage window 36. During the dose setting mode, the actuator assembly, which includes the dose button 30 and clutch 52, moves axially and rotationally with the dose-setting assembly, which includes the flange 38 and the dose-setting screw 32.

Dose-setting screw 32 and flange 38 are fixed rotationally to one another, and rotate and move proximally during dose setting, due to the threaded connection of the dose-setting screw 32 with housing 12. During this dose setting motion, the dose button 30 is rotationally fixed relative to the flange 38 and the dose-setting screw 32 by complementary splines 74 of flange 38 and clutch 52 (FIG. 4), which are urged together by the bias member 68. In the course of dose setting, the dose-setting screw 32, flange 38, clutch 52, and dose button 30 move together relative to the housing 12 in a spiral manner (i.e. simultaneous rotation and axial translation) from a "start" position to an "end" position. This rotation and translation relative to the housing is in proportion to the amount of dose set by operation of the medication delivery device 10.

Once the desired dose is set, device 10 is manipulated so the injection needle 24 properly penetrates, for example, a user's skin. The dose dispensing mode of operation is initiated in response to an axial distal force applied to the proximal face 60 of dose button 30. The axial force is applied by the user directly to dose button 30. This causes axial movement of the actuator assembly (dose button 30 and clutch 52) in the distal direction relative to housing 12.

The axial shifting motion of the actuator assembly compresses biasing member 68 and reduces or closes the gap between dose button 30 and the tubular flange 38. This relative axial movement separates the complementary splines 74 on clutch 52 and flange 38, and thereby disengages the dose button 30 from being rotationally fixed to the flange 38 and the dose-setting screw 32. In particular, the dose-setting screw 32 is rotationally uncoupled from the dose button 30 to allow backdriving rotation of the dose-setting screw 32 relative to the dose button 30 and the housing 12. Also, while the dose-setting screw 32 and flange 38 are free to rotate relative to the housing 12, the dose button 30 is held from rotating relative to the housing 12 by the user's engagement of dose button 30 by pressing against it.

As dose button 30 and clutch 52 are continued to be axially plunged without rotation relative to housing 12, dose-setting screw 32 screws back into housing 12 as it spins relative to dose button 30. The dose markings that indicate the amount still remaining to be injected are visible through window 36. As dose-setting screw 32 screws down distally to advance sleeve 34, drive member 28 is advanced distally to push piston 26 through reservoir 20 and expel medication through needle 24.

During the dose dispensing operation, the amount of medicine expelled from the medication delivery device is proportional to the amount of rotational movement of the dose-setting screw 32 relative to the housing 12 as the dose-setting screw 32 screws back into housing 12. In some embodiments, because the dose button 30 is rotationally fixed relative to the housing 12 during the dose dispensing mode, the amount of medicine expelled from the medication delivery device may be viewed as being proportional to the amount of rotational movement of the dose-setting screw 32 relative to the dose button 30 as the dose-setting screw 32 screws back into housing 12. The injection is completed when the internal threading of dose-setting screw 32 has reached the distal end of the corresponding outer threading of sleeve 34 (FIG. 4). Device 10 is then once again arranged in a ready state or zero dose position as shown in FIGS. 2 and 4.

As discussed above, the dose delivered may be derived based on the amount of rotation of the dose-setting assembly (flange 38 and dose-setting screw 32) relative to the actuator assembly (clutch 52 and dose button 30) during dose delivery. This rotation may be determined by detecting the incremental movements of the dose-setting assembly which are "counted" as the dose-setting assembly is rotated during dose delivery.

Further details of the design and operation of an exemplary delivery device 10 may be found in U.S. Pat. No. 7,291,132, entitled Medication Dispensing Apparatus with Triple Screw Threads for Mechanical Advantage, the entire disclosure of which is hereby incorporated by reference herein. Another example of the delivery device is an auto-injector device that may be found in U.S. Pat. No. 8,734,394, entitled "Automatic Injection Device With Delay Mechanism Including Dual Functioning Biasing Member," which is hereby incorporated by reference in its entirety, where such device being modified with one or more various sensor systems described herein to determine an amount of medication delivered from the medication delivery device based on the sensing of relative rotation within the medication delivery device. Another example of the delivery device is a reusable pen device that may be found in U.S. Pat. No. 7,195,616, entitled "Medication Injector Apparatus with Drive Assembly that Facilitates Reset," which is hereby incorporated by reference in its entirety, where such device being modified with one or more various sensor systems described herein to determine an amount of medication delivered from the medication delivery device based on the sensing of relative rotation within the medication delivery device.

Described herein is a dose detection system that may be operable to determine the amount of dose delivered based on relative rotation between a dose setting member and the device body. The dose detection system utilizes a dose setting and/or delivery member, such as the flange 38, screw 32, or a combination of both as a monolithic unit, attached to the device body and rotatable relative to the device body about an axis of rotation during dose delivery. A sensed element is attached to and rotationally fixed with the dose setting member. An actuator is attached to the device body and is held against rotation relative to the device body during dose delivery. The sensed element thereby rotates relative to the actuator during dose delivery in relation to the amount of dose delivered.

In some embodiments, the dose detection system comprises a rotational sensor attached to the actuator assembly and a sensed element that includes surface features that are equally radially spaced about the axis of rotation of the sensed element.

In some embodiments, the dose detection systems may include a sensor and a sensed component attached to components of the medication delivery device. The term "attached" encompasses any manner of securing the position of a component to another component or to a member of the medication delivery device such that they are operable as described herein. For example, a sensor may be attached to a component of the medication delivery device by being directly positioned on, received within, integral with, or otherwise connected to, the component. Connections may include, for example, connections formed by frictional engagement, splines, a snap or press fit, sonic welding or adhesive.

The term "directly attached" is used to describe an attachment in which two components, or a component and a member, are physically secured together with no intermediate member, other than attachment components. An attachment component may comprise a fastener, adapter or other part of a fastening system, such as a compressible membrane interposed between the two components to facilitate the attachment. A "direct attachment" is distinguished from attachment where the components/members are coupled by one or more intermediate functional members.

The term "fixed" is used to denote that an indicated movement either can or cannot occur. For example, a first member is "fixed rotationally" with a second member if the two members are required to move together in rotation. In one aspect, a member may be "fixed" relative to another member functionally, rather than structurally. For example, a member may be pressed against another member such that the frictional engagement between the two members fixes them together rotationally, while the two members may not be fixed together absent the pressing of the first member.

Various sensor arrangements are contemplated herein. In general, the sensor arrangements comprise a sensor and a sensed component. The term "sensor" refers to any component which is able to detect the relative position or movement of the sensed component. The sensor may be used with associated electrical components to operate the sensor. The "sensed component" is any component for which the sensor is able to detect the position and/or movement of the sensed component relative to the sensor. For the dose detection system, the sensed component rotates relative to the sensor, which is able to detect the rotational movement of the sensed component. The sensor may comprise one or more sensing elements, and the sensed component may comprise one or more sensed elements. The sensor detects the movement of the sensed component and provides outputs representative of the movement of the sensed component.

Illustratively, the dose detection system includes an electronics assembly suitable for operation of the sensor arrangement as described herein. The medication delivery device may include a controller that is operably connected to the sensor to receive outputs from the sensor. The controller begins receiving generated signals from the sensor indicative of counts from first to last one for a total number of counts that is used for determining total displacement, e.g. angular displacement. In the case of detecting an angular movement of a dose-setting assembly, the controller may be configured to receive data indicative of the angular movement of the dose-setting assembly that can be used to determine from the outputs the amount of dose delivered by operation of the medication delivery device. The controller may be configured to determine from the outputs the amount of dose delivered by operation of the medication delivery device. The controller may include conventional components such as a processor, power supply, memory, microcontrollers, etc. Alternatively, at least some components may be provided separately, such as by means of a computer, smart phone or other device. Means are then provided to operably connect the external controller components with the sensor at appropriate times, such as by a wired or wireless connection.

Figure 5:
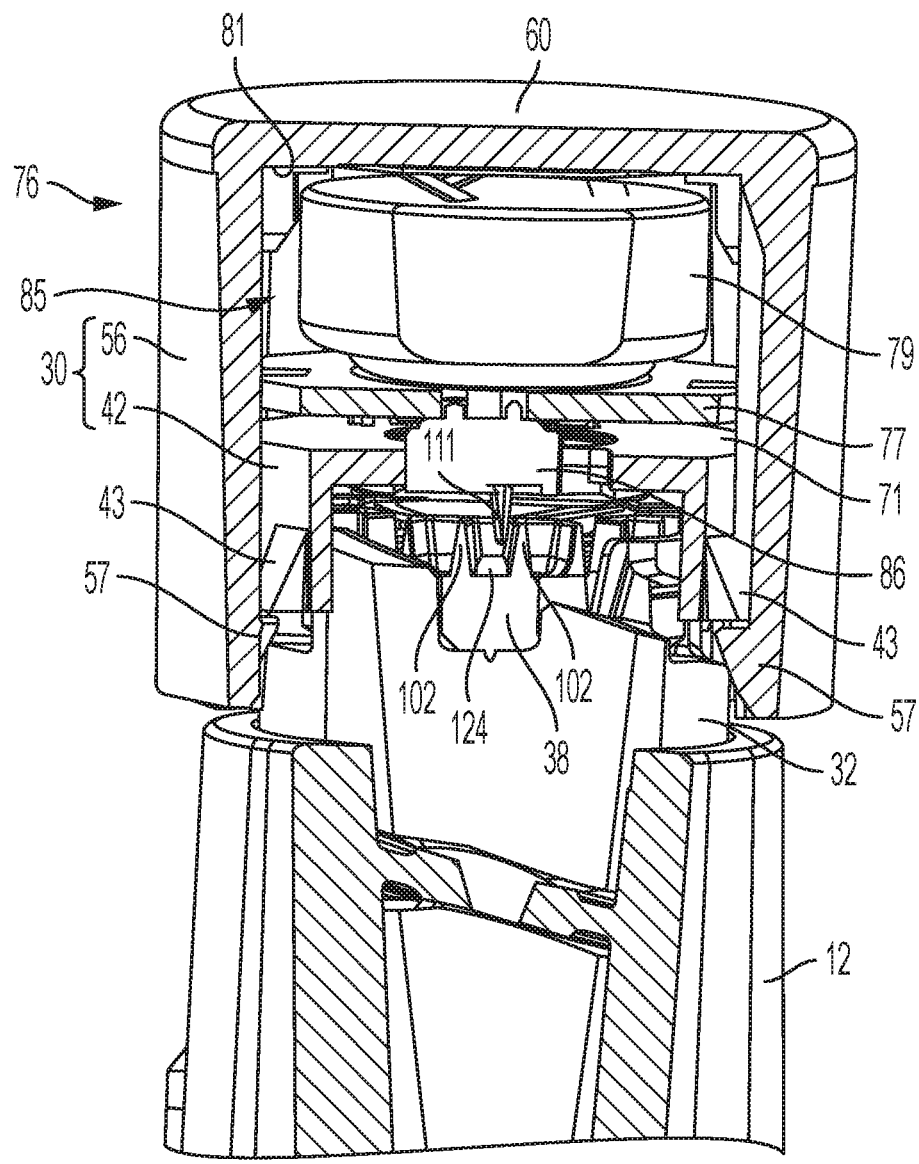
FIG. 5 is a partial cutaway view of a proximal end of the medication delivery device of FIG. 1, showing components of the dose detection system.
Figure 6:
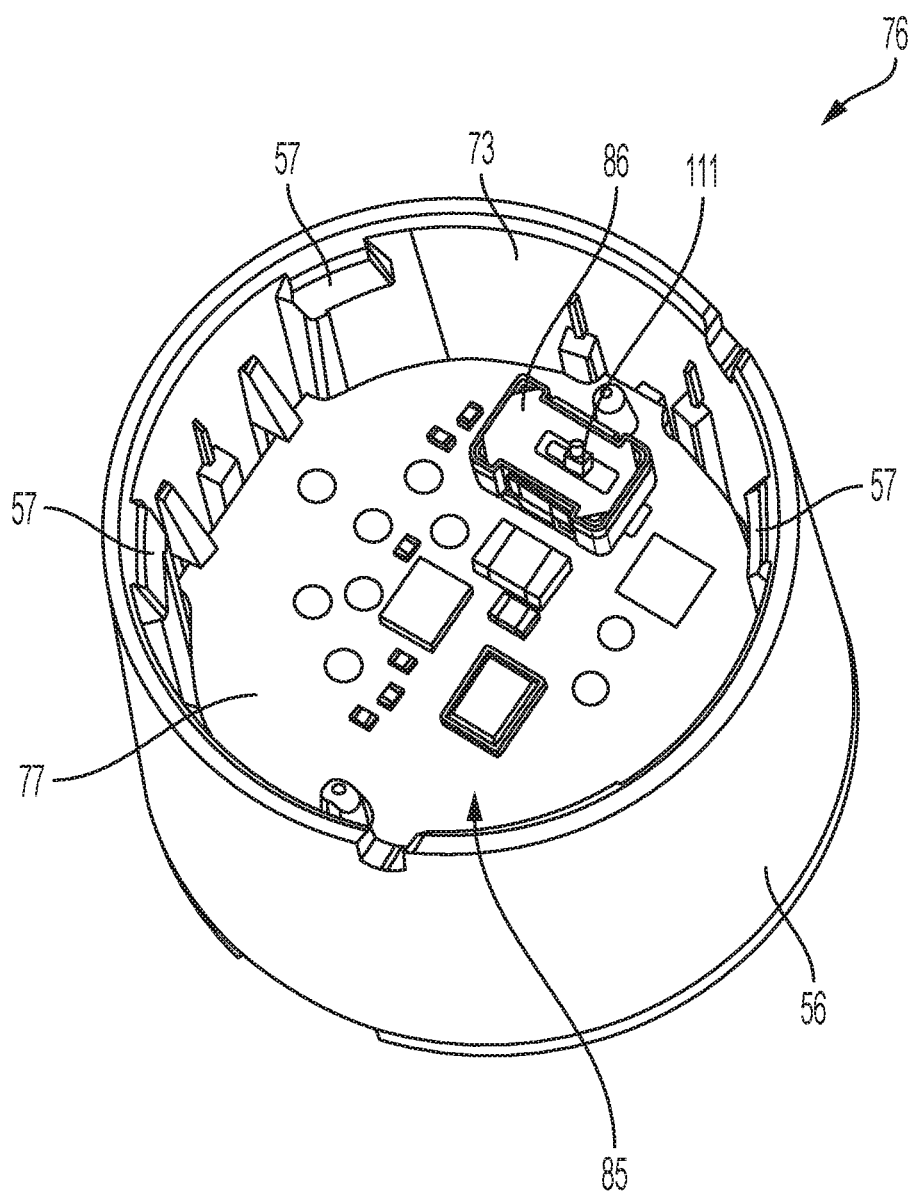
FIG. 6 is an underside view of a portion of the dose button of FIG. 1, showing a printed circuit board held within the dose button cover.
Figure 7:
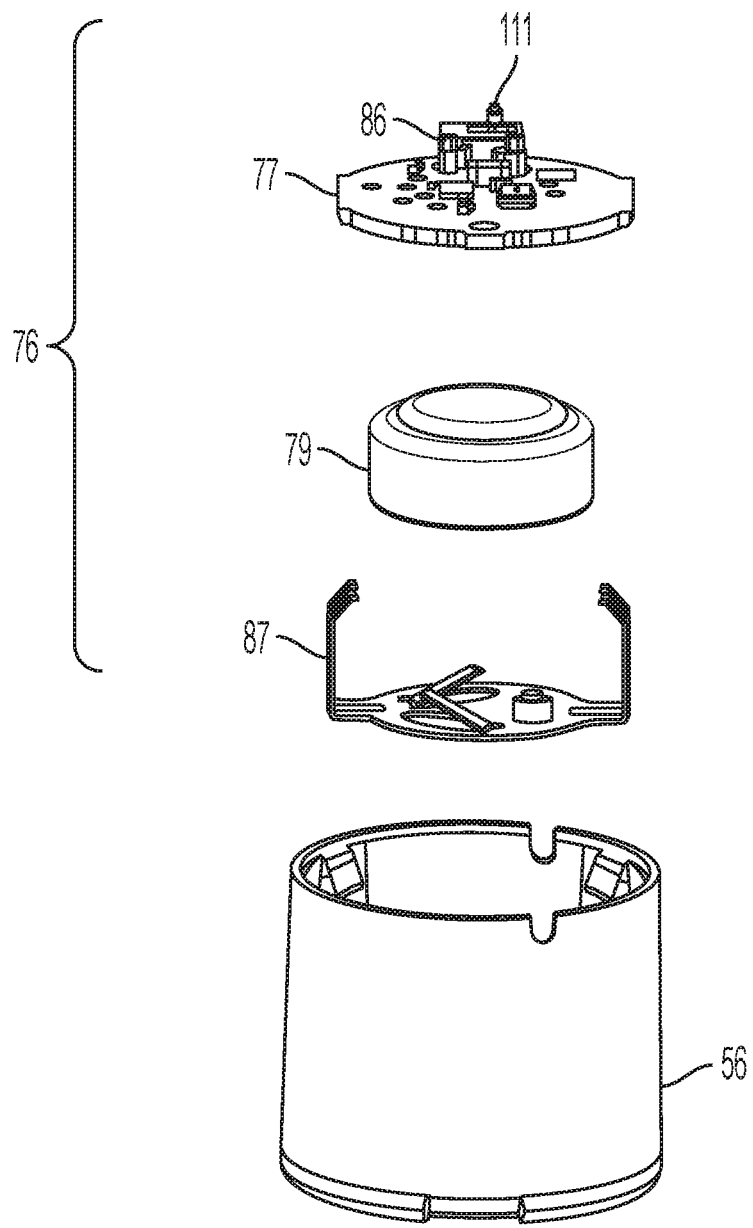
FIG. 7 is an exploded view of the portion of the dose button cover shown in FIG. 6.

According to one aspect, the electronics assembly includes a sensor arrangement including one or more sensors operatively communicating with a processor for receiving signals from the sensor representative of the sensed rotation. An exemplary electronics assembly 76 is shown in FIGS. 5-7 and can include a sensor 86, and a printed circuit board (PCB) 77 having a plurality of electronic components. The printed circuit board may be a flexible printed circuit board. The circuit board of the electronics assembly 76 may include a microcontroller unit (MCU) as the controller comprising at least one processing core and internal memory. The electronics assembly may include a power source 79, e.g. a battery, illustratively a coin cell battery, for powering the components. The controller of electronics assembly 76 may include control logic operative to perform the operations described herein, including detecting the angular movement of the dose-setting assembly during dose setting and/or dose delivery and/or detecting a dose delivered by medication delivery device 10 based on a detected rotation of the dose-setting assembly relative to the actuator assembly. Many, if not all of the components of the electronics assembly, may be contained in a compartment 85 within the dose button 30. In some embodiments, the compartment 85 may be defined between a proximal surface 71 of support 42 of the dose button and a distal surface 81 of the cover 56 of the dose button. In the embodiment shown in FIG. 5, the electronics assembly 76 is permanently integrated within the dose button 30 of the delivery device. In other embodiments, the electronics assembly is provided as a module that can be removably attached to the actuator assembly of the medication delivery device.

An underside view of the electronics assembly 76 held within the cover 56 is shown in FIG. 6, and an exploded view of the electronics assembly 76 is shown in FIG. 7. As shown in FIGS. 6 and 7, the electronics assembly 76 may include a printed circuit board (PCB) 77 and a sensor 86 having a contact surface 111. As shown in FIG. 7, the electronics assembly 76 may also include a battery 79 and a battery cage 87. Other sensors described herein, such as, for example, a magnetic sensor, may not include a contact surface but operate in a non-contact manner.

Figure 10:
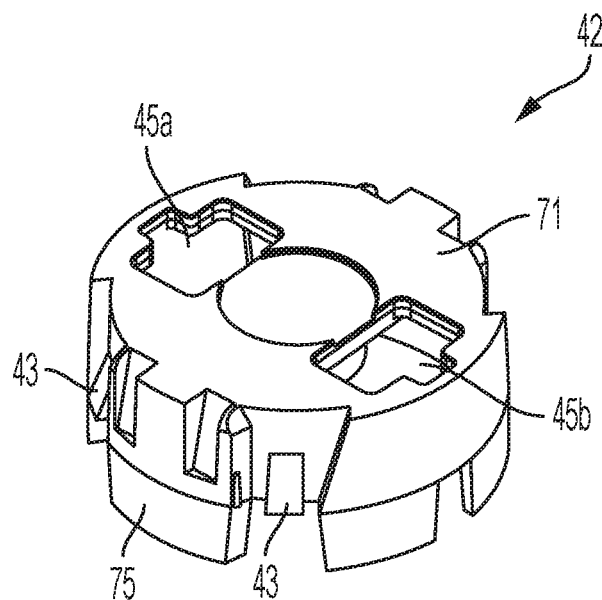
FIG. 10 is a perspective view of a dose button support.
Figure 11:
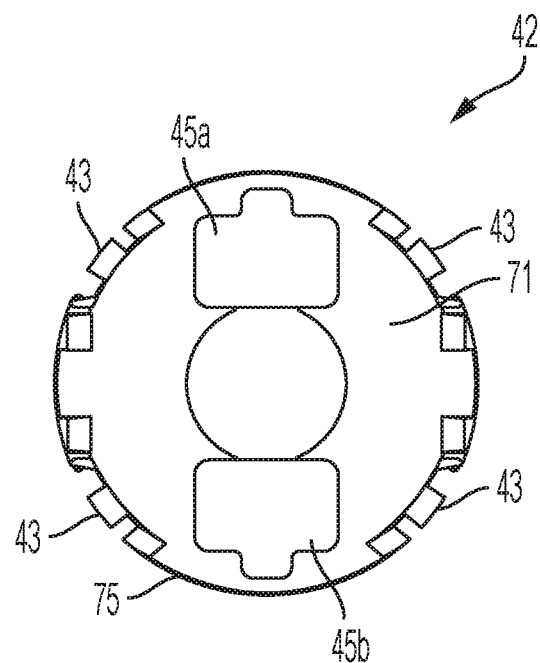
FIG. 11 is a top down view of the dose button support of FIG. 10.

In some embodiments, at least a portion of the sensor 86 extends out of the compartment 85 of the dose button 30. As best seen in FIGS. 10 and 11, the proximal face 71 of the support 42 of the dose button 30 may include one or more openings (shown as first and second openings 45a, 45b) through which the sensor 86 can extend axially through. In some embodiments, during assembly of the medication delivery device, the contact surface 111 of the sensor 86 is passed axially through either of the openings 45a, 45b of the support 42. This may permit the contact surface 111 of the sensor to interact with a component that is external to the compartment 85 of the dose button 30. In some embodiments, while only one of the openings (such as first opening 45a) in the support 42 is needed to accommodate a sensor, the second opening 45b may be provided, e.g. for symmetry of the support component, which help with manufacturing of the component and/or assembly of the component with the medication delivery device by allowing the sensor to be placed in either opening depending on the angular orientation of the support 42. When the sensor lacks a contact surface, the sensor may be positioned over the openings 45a, 45b without any sensor portion extending through the opening or with a portion extending through the opening but not configured to engage the sensed component.

The controller of electronics assembly 76 may be operative to store the total angular movement used for determining dose delivery and/or the detected dose delivery in local memory (e.g., internal flash memory or on-board EEPROM). The controller may be further operative to wirelessly transmit a signal representative of the total counts, total angular movement, and/or detected dose to an external device, such as a user's mobile device or a remote server. Transmission may, for example, be over a Bluetooth low energy (BLE) or other suitable short or long range wireless communication protocol. Illustratively, the BLE control logic and controller are integrated on the same circuit.

As discussed, according to one aspect, the dose detection system involves detecting relative rotational movement between two assemblies of the medication delivery device. With the extent of rotation having a known relationship to the amount of a delivered dose, the sensor operates to detect the amount of angular movement from the start of a dose injection to the end of the dose injection. For example, in some embodiments, the relationship for a pen injector is that an angular displacement of a dose-setting assembly of 18° is the equivalent of one unit of dose, although other angular relationships are also suitable, such as, for example, 9, 10, 15, 20, 24 or 36 degrees may be used for a unit or a half unit. The sensor system is operable to determine the total angular displacement of a dose setting member during dose delivery. Thus, if the angular displacement is 90°, then 5 units of dose have been delivered.

The angular displacement is determined by counting increments of dose amounts as the injection proceeds. For example, a sensing system may use a repeating pattern of a sensed element, such that each repetition is an indication of a predetermined degree of angular rotation. Conveniently, the pattern may be established such that each repetition corresponds to the minimum increment of dose that can be set with the medication delivery device.

The dose detection system components may be permanently or removably attached to the medication delivery device. In some embodiments, at least some of the dose detection system components are provided in the form of a module that is removably attached to the medication delivery device. In other embodiments, the dose detection system components are permanently attached to the medication delivery device.

In some embodiments, a sensor may detect, during dose delivery, the relative rotation of a sensed component that is rotationally fixed to the dose-setting screw 32, from which is determined the amount of a dose delivered by the medication delivery device. In an illustrative embodiment, a rotational sensor is attached, and rotationally fixed, to the actuator assembly. The actuator assembly does not rotate relative to the device housing during dose delivery.

In some embodiments, a sensed component is attached, and rotationally fixed, to the dose-setting screw 32, which rotates relative to the dose button 30 and the device housing 12 during dose delivery. In some of the embodiments described herein, the sensed component includes a ring structure having a plurality of proximally extending projections circumferentially disposed relative to one another. Projections are shaped and sized to deflect a movable element of the rotational sensor. One illustrative embodiment of such a sensed component is tubular flange 38, best seen in FIGS. 3, 5, 8, and 9. Embodiments described herein may be provided for a module that is removably attachable to the dose button of the delivery device or integrated within the dose button of the delivery device.

During dose delivery, dose-setting screw 32 is free to rotate relative to dose button 30. In the illustrative embodiment, the electronics assembly 76 is rotationally fixed with the dose button 30 and does not rotate during dose delivery.

As seen in FIGS. 2, 3 and 5, the dose button 30 comprises a cover 56 coupled to a support 42. An electronics assembly 76 may be at least partially contained within a compartment 85 defined between the cover 56 and the support. In some embodiments, the cover and support have corresponding splines that engage with one another to couple the cover and support together. For example, in some embodiments, the cover 56 may couple to the support 42 via one or more snaps 57 on the cover 56 and corresponding to one or more protrusions 43 on the support. As seen in FIGS. 5 and 6, the snaps 57 on the cover 56 may be directed radially inwardly from an inner circumferential sidewall 73. As seen in FIGS. 5, 10 and 11, the protrusions 43 on the support 42 may be directed radially outwardly from an outer circumferential sidewall 75 of the support 42. The protrusions 43 may form a triangular ramp shape.

The snaps 57 on the cover 56 are configured to snap over and mate with the protrusions 43 on the support to couple the cover to the support. In some embodiments, the protrusion on the support comprises a continuous annular protrusion around the outer circumferential sidewall of the support. The cover 56 may attach to the support 42 via frictional engagement, interference fit or any other suitable fit. In some embodiments, the cover 56 is permanently fixed to the support 42 during assembly, e.g. via ultrasonic welding, adhesive, or other suitable fixation approach.

As seen in FIGS. 8 and 9, the tubular flange 38 may include a plurality of axially directed teeth 102 that may be equally radially spaced about a rotation axis and may be arranged to correlate to the equivalent of one or incremental unit of dose. In this illustrative embodiment, the tubular flange 38 includes 20 teeth 102 that are equally rotationally spaced from one another, such that the rotation distance between two adjacent teeth corresponds to 18 degrees of rotation. Thus, with the tubular flange 38 of FIG. 8, 18 degrees of rotation of the tubular flange 38 may be used to represent one dosage unit or a half dosage unit. It should be appreciated that, in other embodiments, different total numbers of teeth may be used to create other angular relationships, such as, for example, 9, 10, 15, 18, 20, 24 or 36 degrees may be used for a unit or 0.5 unit.

A recess 124 may be defined between each pair of adjacent teeth 102. Each tooth 102 may have an approximately triangular shaped profile, each having a surface 120 against which a contact surface 111 of a sensor may slide.

In some embodiments, the sensor for detecting rotation of the tubular flange includes a movable element that has a contact portion capable of resting against the teeth of the tubular flange and is spring-biased such that the contact surface is configured to slide against and over the teeth during rotation of the flange relative to the actuator assembly during dose delivery. The sensor is responsive to the movement of the contact portion over the teeth and generates signals corresponding to the flange. A controller is responsive to the signals generated by the sensor to determine a dose count for determining the dosage delivered based on the detected rotation of the flange relative to the actuator assembly during dose delivery.

The contact surface may be biased against the physical features of the tubular flange to ensure proper contact between the contact surface and the physical features during rotation. In one embodiment, the movable element is a resilient member having one portion attached to the actuator at a location displaced from the contact surface. In one example, the movable element is a following member comprising a beam attached at one end to the actuator and having the contact surface at the other end. The beam is flexed to urge the contact surface in the direction of the surface features. Alternatively, the movable element may be biased in any of a variety of other ways. In addition to the use of a resilient beam, the biasing may be provided, for example, by use of a spring component. Such spring component may for example comprise a compression, tension, or torsion coil spring. In yet other embodiments, the movable element may be biased against the surface features of the sensed element by a separate resilient member or spring component bearing against the movable element.

FIG. 5 depicts an illustrative embodiment of a sensor 86 having a contact surface 111 interacting with teeth 102 of a tubular flange 38. As the flange 38 rotates relative to the dose button 30 during delivery, the teeth 102 of the flange contact and slide against the contact surface 111 of the sensor 86, causing the contact surface 111 to move in an oscillating manner. The movement of the contact surface 111 may be a combination of axial and lateral movement as the contact surface 111 slides into and out of the recesses 124 defined between the teeth 102 of the flange 38. The sensor 86 may be configured to track the movement of the contact surface 111 and associate the movement with an output signal that is sent to a controller. In an embodiment, the sensor comprises a switch defining the contact surface 111 that moves in an oscillating manner when sliding against the protrusions during rotation of the tubular body relative to the dose button to change the state of the switch between open and closed states during the dose dispensing mode.

As alternative to teeth on the tubular flange, surface features that interact with the sensor may comprise anything detectable by the sensor. The sensor arrangement may be based on a variety of sensed characteristics, including tactile, optical, electrical and magnetic properties, for example. In the illustrative embodiments shown in the figures, the surface features are physical features which allow for detection of incremental movements as the dose-setting assembly rotates relative to the actuator assembly. In alternative embodiments, the sensor may be a piezoelectric sensor, a magnetic sensor such as a Hall effect sensor, where the teeth have magnets or distinguishable magnetic properties, a capacitive or inductive sensor with the teeth have metallic properties, an accelerometer for detecting vibration, e.g. of a ratcheting or other detent mechanism, where vibration can be correlated with rotational movement, an optical sensor such as a reflective sensor, an interrupter sensor, or an optical encoder, or any other sensor suitable for sensing rotation of a first component relative to a second component.

In some embodiments, when a user presses axially on face 60 of the dose button 30, the dose button 30 advances distally relative to the housing 12, compressing spring 68. Continued pressing of the dose button 30 distally results in back driving of the dose-setting screw 32 in a spiral direction relative to housing 12. As a result, the dose-setting screw 32 and flange 38 are driven to rotate by the axially pressing upon the dose button 30. In some embodiments, the dose detection system is operable for dose detection only while the dose button is being pressed.

In some embodiments, the electronics assembly may include a clock or timer to determine the time elapsed between counts caused by trigger of the rotational sensor from the surface features of the sensed element. When no counts have been detected by the controller after a period of time this may be used to indicate that the dose has completed.

In some embodiments, a single sensing system may be employed for both dose detection sensing and wake-up activation. For example, upon the initial sensing of rotation of the sensed element by the sensor, the controller is configured to allow wake-up or activation of the electronics assembly to a greater or full power state. The wake-up feature is configured to allow power transmission from the power source (shown as battery) for powering up the electronic components for dose sensing in order to minimize inadvertent power loss or usage when a dose dispensing event is not occurring. In other embodiments, a separate wake-up switch may be provided and arranged within the dose button housing and triggered when the dose button is in its distal position. After activation of the electronics assembly, the controller begins receiving generated signals from the rotational sensor indicative of counts from first to last one for a total number of counts that is used for determining total angular displacement and thus the amount of dose delivered.

In some embodiments, the electronics assembly may have a controller that is configured to receive an output signal from a rotational sensor. The controller of the electronics assembly may be programmed to convert the intermediate signal to a conditioned digital signal, which may be a single step/square wave with a predetermined width representing a predetermined time. In some embodiments, output signals that are less than a predetermined level may be filtered out and ignored.

According to one aspect, a user may receive digital feedback regarding how much medication remains within the medication delivery device. When the medication level of the medication delivery device becomes low, the user may receive an alert from the medication delivery device and/or from an external device informing the user of the low medication level. For example, the user may receive the alert from a mobile device, e.g. from an app, text message or SMS. An alert may be visual, auditory, tactile (e.g. a vibration) or any combination thereof.

In some embodiments, the user may be advised to refill their medication and/or, for re-useable medication delivery device, replace the medication cartridge with a new cartridge. In some embodiments, a refill request may be automatically sent to a pharmacy when a medication level is detected to be low.

The method by which medication level is determined may be accomplished in different ways. In some embodiments, an external device stores a record of the level of medication remaining in a medication delivery device. The medication delivery device may send communications to the external device, informing the external device of the dosage that was delivered from each medication delivery event. The medication delivery device may determine such dosage information from the sensor described above. The external device may then calculate and store the amount of medication remaining after each medication delivery event. For example, the external device may subtract the delivered dosage amount from the last-known remaining amount of medication.

In some embodiments, the information regarding the amount of medication remaining in a medication delivery device may be calculated and/or stored by the medication delivery device itself. The medication delivery device may then communicate to an external device how much medication remains in the medication delivery device.

In some embodiments, tracking the amount of medication remaining in a medication delivery device may be used for patient adherence purposes. A user, caretaker, healthcare provider, insurance payer, and/or a company creating the medication may wish to monitor whether the user is taking the medication at the prescribed amounts and/or times. In some embodiments, such information may be used in conjunction with other devices to improve treatment for the patient. For example, the medication delivery device may be used in conjunction with a glucose meter. Dosages delivered to a patient may be paired with glucose level information to determine information such as efficacy of the medication, efficacy of the patient's regimen, etc. Such information may help to improve patient treatment, e.g. by suggesting possible ways to improve the patient's regimen.

According to one aspect, a medication delivery device may have the ability to assist a user with finding the location of the medication delivery device. The inventors have appreciated that a user may, at times, have trouble finding their medication delivery device, particularly if it is portable and can be used in different locations. The inventors have recognized the need for a device location assist feature to help the user locate the device.

In some embodiments, the location of a medication delivery device is tracked by one or more mobile devices. For example, a medication delivery device may be configured to communicate with one or more mobile devices or other external devices such as a remote server. The communication may be one-way communication or two-way communication.

In some embodiments, the medication delivery device periodically advertises information such as a unique identifier. A mobile device may periodically scan for medication delivery devices, and if the advertising medication delivery device is in communication range with the mobile device, the mobile device would receive the communication from the medication delivery device. The mobile device, which may have a built-in GPS or other location-identifying ability, may then associate a location with each received communication. Particularly if the communication protocol between the medication delivery device and the mobile device is a short distance communication protocol, such as Bluetooth, the mobile device may assign the mobile device's own present location, or a radius around the mobile device's own present location, as the location of the medication delivery device. In some embodiments, when the mobile device no longer receives communications from the medication delivery device, indicating that perhaps the medication delivery device has been moved out of communication range from the mobile device, the mobile device stores a last-known location of the medication delivery device, which may be when the mobile device last received communication from the medication delivery device. This last-known location may be presented to a user to help the user determine the location of the medication delivery device.

In some embodiments, when a mobile device is brought into communication range with a medication delivery device, the mobile device may alert a user that a medication delivery device is nearby. This may be used to help the user physically find the medication delivery device.

In some embodiments, when a mobile device senses that a medication delivery device is no longer in communication range with the mobile device (e.g. the mobile device does not receive an advertisement from the medication delivery device within an expected time period), the mobile device may alert the user the medication delivery device is no longer nearby, or at least no longer close to the mobile device itself. Such a feature may help the user to avoid forgetting to bring the medication delivery device when the user leaves a location.

In some embodiments, multiple mobile devices may cooperate to help locate a medication delivery device. For example, a group of mobile devices may be configured to scan periodically for medication delivery devices. When one of the mobile devices locates a medication delivery device (e.g. by sensing that the medication delivery device is in communication range), the mobile device may communicate the identity and/or location of the found medication delivery device to the rest of the mobile devices. This may be used, for example, in a household setting where members of the household each have their own mobile device.

In some embodiments, the medication delivery device may include a built-in speaker. To help a user find the medication delivery device, the speaker may be triggered by the user to emit a sound. In some embodiments, a user may use a mobile device to trigger the speaker to emit a sound.

In some embodiments, the medication delivery device itself may have a built-in GPS or other location-identifying ability. The medication delivery device may communicate its location to a mobile device or other external device, such as directly to a remote server.

According to one aspect, the date, and in some embodiments, time, at which a medication delivery device is used for the first time is tracked.

One example use case for such a feature is determining medication expiration. For example, in some embodiments, a medication delivery device may communicate to an external device that user has opened, turned on, or otherwise activated the medication delivery device for the first time. The external device may check whether the medication has expired, by, for example, looking up an identification number of the medication delivery device in an expiration date database.

Another example use case for such a feature is to assist in supply chain management. Knowing when a specific medication delivery device has been activated for the first time may give a manufacturer important supply chain information, for example, how long it takes a medication delivery device to reach a user and be used by a user after the manufacturer has released it for sale. When communicating first use to an external device, the medication delivery device may also communicate its specific identification number to permit a manufacturer to associate the information to a known device and store the information in a database. The information can be categorized by device type, geography, etc.

In some embodiments, the time elapsed from first use of a medication delivery device may be monitored. With some types of medications and medication delivery devices, the medication in a medication delivery device expires after a certain amount of time has elapsed since the medication delivery device was first used to deliver an amount of the medication. This may apply in particular to multi-dose type medication delivery devices. As such, the medication delivery device may detect when the user has actuated the device to deliver medication for the first time. In some embodiments, the device may then begin an internal timer countdown and alert a user that the medication has expired when the timer reaches a predetermined time. Examples of an alert include turning on, off, or blinking a light and/or using a light of a certain color, an auditory sound, a vibration, or any combination thereof. In some embodiments, the medication delivery device may prevent the user from actuating the device, e.g. with a physical and/or electrical lockout that makes delivery impossible. In some embodiments, when the medication delivery device detects that the user has actuated the device to deliver medication for the first time, the medication delivery device may communicate to an external device that first time delivery has occurred. The external device may then begin a countdown to the expiration of the medication. When the countdown as completed, the external device may send an alert to the user and/or communicate to the medication delivery device that the medication has expired.

According to one aspect, a temperature of the medication may be monitored. Medication temperature may be monitored directly or indirectly. One example of direct measurement includes placing a temperature sensor in actual contact with the medication. One example of indirect measurement includes using a temperature sensor to measure the temperature of a region or component close to the medication to approximate what the actual temperature of the medication is. For example, in one embodiment, a temperature sensor is located at the PCB of a medication delivery device. Another example of indirect measurement includes directly measuring the temperature of a material within the medication delivery device that behaves similarly to the actual medication when exposed to various temperature environments.

Temperature measurements may occur periodically. Information relating to the measured temperature may be stored within the medication delivery device, may be communicated to an external device each time a measurement occurs or in batches, or any combination thereof.

When the medication delivery device sensors that the measured temperature is outside an acceptable temperature range, referred to herein as a "temperature excursion," a variety of responses may occur. In some embodiments, the medication delivery device alerts the user directly and/or communicates the information to one or more external devices, which may in turn alert the user. The alert may occur in real-time when the temperature excursion is detected, or may occur the next time the user uses the medication delivery device. In some embodiments, when a temperature excursion is detected, the medication delivery device may store and/or communicate to an external device the time and/or date of the temperature excursion, as well as the measured temperature.

According to one aspect, a medication delivery device and/or an external program that communicates with the medication delivery device, such as a mobile device app, may include security features for controlling wireless communication between the medication delivery device and an external device. In some embodiments, the medication delivery device includes a bond management feature that prevents unwanted access to the medication delivery device from third parties. In this bond management feature, a user has already paired their medication delivery device to the user's mobile device, which may be running an app that is specialized for use with the medication delivery device. If a different mobile device tries to connect with the medication delivery device, the user may receive a notification that a third party is attempting to connect with the medication delivery device. The user may grant or deny permission for the third party to connect with the medication delivery device. In some embodiments, this setting may be "remembered" by the app and/or medication delivery device to avoid repeated notifications. In some embodiments, the app may be configured to include a menu that allows a user to change past authorization settings, e.g. to grant access to a previously denied third party mobile device, or to deny access to a previously approved third party mobile device.

According to one aspect, a user may be notified by an external device or by the medication delivery device itself if the medication delivery device is subject to a recall. In some embodiments, the medication delivery device broadcasts its unique identification number to an external device which may communicate with a remote server that has a database that associates recall information with the identification number. The medication delivery device may communicate directly with the remote server itself.

In some embodiments, an external device such as a mobile device alerts a user that the medication delivery device and/or the medication within the device is subject to a recall and should not be used. The alert may take different forms, including a message displayed by an app running on the mobile device, via text message, via SMS, via email, or any combination thereof.

In some embodiments, the medication delivery device may be instructed by the remote server and/or an intermediate external device such as a mobile device to display an alert informing the user that the medication delivery device and/or medication is subject to a recall and should not be used. In some embodiments, the medication delivery device may activate a physical and/or electrical lockout that prevents the device from being used.

According to one aspect, the medication delivery device may be used to detect failure to administer a dose in accordance with the user's prescribed regimen. For example, if a user accidentally administers two doses at once or too close in time, an external device or the medication delivery device itself will inform the user of the error. As other examples, a user may have accidentally or intuitionally skipped a dose, or may have used an incorrect dose.

Detection of these types of errors may give the user an opportunity to take remedial measures. The external device may provide suggestions to the user for remedial measures, may inform the user's healthcare provider, may connect the user to the healthcare provider, or any combination thereof.

In some embodiments, such errors are able to be monitored because the medication delivery device may be able to detect delivery of medication and may be able to detect the dosage that was delivered. The medication delivery device may communicate such information out to an external device.

Either the external delivery device or the medication delivery device itself may then determine whether such administrations were proper. In some embodiments, an external device or the medication delivery device itself may compare timings and dosages of actual administrations against expected administrations. If the actual administrations do not match with the expected administrations, then the external device and/or the medication delivery device may inform the user, e.g. that they have missed a dose, administered too much or too little of a dosage, or any combination thereof. In one illustrative embodiment, a medication delivery device communicates dosage amounts and delivery times to a mobile device. The mobile device then communicates with a remote server to determine whether this actual administration matches with an expected prescribed regimen. If the actual administration does not match with the expected regimen, then the mobile device alerts the user to an administration error. In situations with a missed dose, the remote server may communicate with the mobile device the inform the mobile device that a dosage should have been administered. If the mobile device has not received information from the medication delivery device indicating that the dosage was administered, the mobile device may then send an alert to the user reminding the user to take their medication.

The shown device is a reusable pen-shaped medication injection device, generally designated, which is manually handled by a user to selectively set a dose and then to inject that set dose. Injection devices of this type are well known, and the description of device is merely illustrative as the sensing system can be adapted for use in variously configured medication delivery devices, including differently constructed pen-shaped medication injection devices, differently shaped injection devices, and infusion pump devices. The medication may be any of a type that may be delivered by such a medication delivery device. Device is intended to be illustrative and not limiting as the sensing system described further below may be used in other differently configured devices.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

While various embodiments have been described, it will be apparent to those of ordinary skill in the art that many more embodiments and implementations are possible. Accordingly, the embodiments described herein are examples, not the only possible embodiments and implementations. Furthermore, the advantages described above are not necessarily the only advantages, and it is not necessarily expected that all of the described advantages will be achieved with every embodiment.

Various aspects are described in this disclosure, which include, but are not limited to, the following aspects:

1. A medication delivery device comprising: a housing; an outlet; a dose button that is axially translatable relative to the housing to activate a dose dispensing mode in which medication is dispensed out of the outlet, the dose button comprising a support and a cap coupled to the support; a compartment defined between the support and the cap; a tubular body that rotates relative to the housing during the dose dispensing mode; and an electronics assembly, the electronics assembly including a sensor configured to sense rotation of the tubular body and a controller configured to receive a signal from the sensor, and wherein at least a portion of the electronic assembly is positioned within the compartment.

2. The medication delivery device of aspect 1, wherein the tubular body rotates relative to the dose button during the dose dispensing mode, and the sensor is configured to sense rotation of the tubular body relative to the dose button.

3. The medication delivery device of any one of aspects 1-2, wherein the dose button is rotatable relative to the housing during a dose setting mode and rotates with the tubular body during the dose setting mode.

4. The medication delivery device of any one of aspects 1-3, wherein the support includes an opening through which at least a portion of the sensor extends.

5. The medication delivery device of aspect 4, wherein the opening is located on a proximal face of the support.

6. The medication delivery device of any one of aspects 1-5, wherein the support includes a plurality of protrusions extending radially outwardly, the protrusions being engaged with the cap to couple the cap to the support.

7. The medication delivery device of any one of aspects 1-6, further comprising a rotatable screw that rotates relative to the housing during a dose setting mode, wherein degree of rotation of the screw during the dose setting mode determines an amount of medication to be dispensed out of the outlet during the dose dispensing mode, the tubular body being rotationally fixed to the rotatable screw.

8. The medication delivery device of aspect 7, wherein the dose button rotates with the rotatable screw and the tubular body during the dose setting mode, and the rotatable screw and the tubular body rotate relative to the dose button during the dose dispensing mode.

9. The medication delivery device of any one of aspects 1-8, wherein the sensor comprises a switch.

10. The medication delivery device of aspect 9, wherein the tubular body comprises a plurality of protrusions and indentations, wherein the switch slides against the protrusions during rotation of the tubular body relative to the dose button during the dose dispensing mode.

11. The medication delivery device of aspect 10, wherein the plurality of protrusions are equally spaced from one another in a circular arrangement.

12. The medication delivery device of aspect 8, wherein the sensor comprises a hall effect sensor.

13. The medication delivery device of aspect 8, wherein the sensor comprises an accelerometer.

14. The medication delivery device of aspect 8, further comprising a clutch, the clutch and the tubular body having complementary splines that couple the dose button to the tubular body during the dose setting mode such that the dose button and the tubular body rotate together during the dose setting mode, wherein the splines of the clutch separate from the splines of the tubular body during the dose dispensing mode to uncouple the dose button from the tubular body to permit the tubular body to rotate relative to the dose button.

15. The medication delivery device of aspect 14, wherein at least a portion of the clutch passes through the tubular body.

16. The medication delivery device of any one of aspects 1-15, wherein the support and the cap have complementary interlocking features that mate the support and the cap together.

17. A method of assembling a medication delivery device comprising: providing a housing; providing an outlet; coupling a tubular body to the housing, the tubular body being configured to rotate relative to the housing during a dose dispensing mode in which medication is dispensed out of the outlet; forming a dose button having a cap and a support by at least partially enclosing an electronics assembly between the cap and the support and attaching the cap to the support, the electronics assembly having a sensor configured to sense rotation of the tubular body; and configuring the dose button to be axially translatable relative to the housing, wherein axially translating the dose button relative to the housing activates the dose dispensing mode.

18. The method of aspect 17, further comprising inserting the sensor at least partially through an opening in the support to permit the sensor to interact with the tubular body.

19. The method of any one of aspects 17-18, further comprising coupling the tubular body to a rotatable screw to rotationally fix the tubular body to the rotatable screw and configuring the rotatable screw to be rotatable relative to the housing during a dose setting mode, wherein degree of rotation of the screw during the dose setting mode determines an amount of medication to be dispensed out of the outlet during the dose dispensing mode.

20. The method of any one of aspects 17-19, further comprising configuring the tubular body to rotate relative to the dose button during the dose dispensing mode, and configuring the sensor to sense rotation of the tubular body relative to the dose button.

21. The method of any one of aspects 17-20, further comprising configuring the dose button to be rotatable relative to the housing during a dose setting mode and to be rotatable with the tubular body during the dose setting mode.

22. The method of aspect 19, further comprising configuring the dose button to be rotatable with the rotatable screw and the tubular body during the dose setting mode, and configuring the rotatable screw and the tubular body to be rotatable relative to the dose button during the dose dispensing mode.

23. The method of any one of aspects 17-22, further comprising providing a switch for the sensor.

24. The method of aspect 23, further comprising providing the tubular body with a plurality of protrusions and indentations, wherein the switch slides against the protrusions during rotation of the tubular body relative to the dose button during the dose dispensing mode.

25. The method of aspect 23, further comprising inserting a clutch at least partially through the tubular body, the clutch and the tubular body having complementary splines that couple the dose button to the tubular body during a dose setting mode such that the dose button and the tubular body rotate together during the dose setting mode, wherein the splines of the clutch separate from the splines of the tubular body during a dose dispensing mode to uncouple the dose button from the tubular body to permit the tubular body to rotate relative to the dose button.

What is claimed is:

1. A medication delivery device comprising:
    a housing having a longitudinal axis;
    an outlet;
    a dose button that is axially translatable relative to the housing to activate a dose dispensing mode in which medication is dispensed out of the outlet, the dose button comprising a support and a cap coupled to the support;
    a compartment defined between the support and the cap;
    a tubular body that rotates relative to the housing during the dose dispensing mode; and
    an electronics assembly, the electronics assembly including a sensor configured to sense rotation of the tubular body and a controller configured to receive a signal from the sensor, wherein the electronics assembly is rotationally fixed relative to the support, wherein at least a portion of the electronics assembly is positioned within the compartment, and wherein the support includes an opening through which at least a portion of the sensor axially extends in a direction parallel to the longitudinal axis of the housing.

2. The medication delivery device of claim 1, wherein the tubular body rotates relative to the dose button during the dose dispensing mode, and the sensor is configured to sense rotation of the tubular body relative to the dose button.

3. The medication delivery device of claim 1, wherein the dose button is rotatable relative to the housing during a dose setting mode and rotates with the tubular body during the dose setting mode.

4. The medication delivery device of claim 1, wherein the opening is a first opening and the support includes a second opening located on a proximal face of the support, wherein each of the openings is configured to receive at least the portion of the sensor, wherein the portion of the sensor axially extends through only one of the openings.

5. The medication delivery device of claim 1, wherein the support includes a plurality of protrusions extending radially outwardly, the protrusions being engaged with the cap to couple the cap to the support.

6. The medication delivery device of claim 1, further comprising a rotatable screw that rotates relative to the housing during a dose setting mode, wherein a degree of rotation of the screw during the dose setting mode determines an amount of medication to be dispensed out of the outlet during the dose dispensing mode, the tubular body being rotationally fixed to the rotatable screw.

7. The medication delivery device of claim 6, wherein the dose button rotates with the rotatable screw and the tubular body during the dose setting mode, and the rotatable screw and the tubular body rotate relative to the dose button during the dose dispensing mode.

8. The medication delivery device of claim 7, wherein the sensor comprises a hall effect sensor.

9. The medication delivery device of claim 7, wherein the sensor comprises an accelerometer.

10. The medication delivery device of claim 7, further comprising a clutch, the clutch and the tubular body having complementary splines that couple the dose button to the tubular body during the dose setting mode such that the dose button and the tubular body rotate together during the dose setting mode, wherein the splines of the clutch separate from the splines of the tubular body during the dose dispensing mode to uncouple the dose button from the tubular body to permit the tubular body to rotate relative to the dose button.

11. The medication delivery device of claim 10, wherein at least a portion of the clutch passes through the tubular body.

12. The medication delivery device of claim 1, wherein the sensor comprises a switch.

13. The medication delivery device of claim 12, wherein the tubular body comprises a plurality of protrusions and indentations, wherein the switch slides against the protrusions during rotation of the tubular body relative to the dose button during the dose dispensing mode.

14. The medication delivery device of claim 13, wherein the plurality of protrusions are equally spaced from one another in a circular arrangement.

15. The medication delivery device of claim 1, wherein the support and the cap have complementary interlocking features that mate the support and the cap together.

16. The medication delivery device of claim 1, wherein the housing further comprises a reservoir including the medication.

17. A method of assembling a medication delivery device comprising:
    providing a housing having a longitudinal axis;
    providing an outlet;

coupling a tubular body to the housing, the tubular body being configured to rotate relative to the housing during a dose dispensing mode in which medication is dispensed out of the outlet;

forming a dose button having a cap and a support by at least partially enclosing an electronics assembly between the cap and the support and attaching the cap to the support, the electronics assembly having a sensor configured to sense rotation of the tubular body, wherein the electronics assembly is rotationally fixed relative to the support, and wherein the support includes an opening through which at least a portion of the sensor axially extends in a direction parallel to the longitudinal axis of the housing; and configuring the dose button to be axially translatable relative to the housing, wherein axially translating the dose button relative to the housing activates the dose dispensing mode.

18. The method of claim 17, wherein the opening is a first opening and the support defines a second opening, wherein each of the openings is configured to receive at least a portion of the sensor, the method further comprising inserting the portion of the sensor at least partially through only one of the openings in the support to permit the sensor to interact with the tubular body.

19. The method of claim 17, further comprising coupling the tubular body to a rotatable screw to rotationally fix the tubular body to the rotatable screw and configuring the rotatable screw to be rotatable relative to the housing during a dose setting mode, wherein a degree of rotation of the screw during the dose setting mode determines an amount of medication to be dispensed out of the outlet during the dose dispensing mode.

20. The method of claim 19, further comprising configuring the dose button to be rotatable with the rotatable screw and the tubular body during the dose setting mode, and configuring the rotatable screw and the tubular body to be rotatable relative to the dose button during the dose dispensing mode.

21. The method of claim 18, further comprising configuring the tubular body to rotate relative to the dose button during the dose dispensing mode, and configuring the sensor to sense rotation of the tubular body relative to the dose button.

22. The method of claim 17, further comprising configuring the dose button to be rotatable relative to the housing during a dose setting mode and to be rotatable with the tubular body during the dose setting mode.

23. The method of claim 17, further comprising providing a switch for the sensor.

24. The method of claim 23, further comprising providing the tubular body with a plurality of protrusions and indentations, wherein the switch slides against the protrusions during rotation of the tubular body relative to the dose button during the dose dispensing mode.

25. The method of claim 23, further comprising inserting a clutch at least partially through the tubular body, the clutch and the tubular body having complementary splines that couple the dose button to the tubular body during a dose setting mode such that the dose button and the tubular body rotate together during the dose setting mode, wherein the splines of the clutch separate from the splines of the tubular body during the dose dispensing mode to uncouple the dose button from the tubular body to permit the tubular body to rotate relative to the dose button.

* * * * *